(12) United States Patent
Sweeney

(10) Patent No.: US 8,805,504 B2
(45) Date of Patent: Aug. 12, 2014

(54) SYSTEM AND METHOD FOR CARDIAC RESYNCHRONIZATION THERAPY CONTROL PARAMETER GENERATION USING VENTRICULAR ACTIVATION SIMULATION AND SURFACE ECG REGISTRATION

(75) Inventor: Michael O. Sweeney, Newton, MA (US)

(73) Assignee: Brigham and Women's Hospital, Boston, MA (US)

( * ) Notice: Subject to any disclaimer, the term of this patent is extended or adjusted under 35 U.S.C. 154(b) by 0 days.

(21) Appl. No.: 13/982,155

(22) PCT Filed: Jan. 31, 2012

(86) PCT No.: PCT/US2012/023256
§ 371 (c)(1),
(2), (4) Date: Jul. 26, 2013

(87) PCT Pub. No.: WO2012/106297
PCT Pub. Date: Aug. 9, 2012

(65) Prior Publication Data
US 2013/0310890 A1    Nov. 21, 2013

Related U.S. Application Data

(60) Provisional application No. 61/462,366, filed on Feb. 1, 2011.

(51) Int. Cl.
*A61N 1/00* (2006.01)
(52) U.S. Cl.
USPC .......................................................... 607/25
(58) Field of Classification Search
USPC .......................................................... 607/25
See application file for complete search history.

(56) References Cited

U.S. PATENT DOCUMENTS

| | | |
|---|---|---|
| 2004/0122479 A1 | 6/2004 | Spinelli et al. |
| 2004/0172079 A1 | 9/2004 | Chinchoy |
| 2004/0193223 A1 | 9/2004 | Kramer et al. |
| 2004/0215252 A1 | 10/2004 | Verbeek et al. |
| 2007/0142871 A1 | 6/2007 | Libbus et al. |
| 2008/0119903 A1 | 5/2008 | Arcot-Krishnamurthy et al. |
| 2008/0306568 A1 | 12/2008 | Ding et al. |
| 2009/0157134 A1 | 6/2009 | Ziglio et al. |
| 2009/0299423 A1 | 12/2009 | Min |
| 2010/0268059 A1 | 10/2010 | Ryu et al. |

OTHER PUBLICATIONS

PCT International Search Report and Written Opinion, PCT/US2010/042337, Mar. 31, 2011.
PCT International Search Report and Written Opinion, PCT/US2012/046907, Oct. 18, 2012.
International Search Report and Written Opinion under date of mailing of Aug. 27, 2012 in connection with PCT/US2012/023256.
Sweeney, Michael O. et al. "Analysis of Ventricular Activation Using Surface Electrocardiography to Predict Left Ventricular Reverse Volumetric Remodeling During Cardiac Resynchronization Therapy." Circulation. Feb. 9, 2010., vol. 121, Issue 5; pp. 626-634.

*Primary Examiner* — Robert N Wieland
(74) *Attorney, Agent, or Firm* — Quarles & Brady, LLP

(57) ABSTRACT

A system and method for cardiac resynchronization therapy ("CRT"] in which a model of baseline cardiac electrical activity, such as a model of global baseline cardiac electrical activity derived from various surface electrocardiograph ("ECG") signals, is utilized to automatically adjust pacing control parameters of a cardiac implantable electrical device ("CIED") are provided. The baseline model is modified with simulated pacing control parameters in an iterative fashion until ventricular electrical asynchrony is minimized. The simulated pacing control parameters resulting in the minimum ventricular electrical asynchrony are used to generate an updated model of ventricular activation, and this updated model is used to generate control parameters for the CIED using a QRS glyph morphological framework.

16 Claims, 3 Drawing Sheets

SYSTEM AND METHOD FOR CARDIAC RESYNCHRONIZATION THERAPY CONTROL PARAMETER GENERATION USING VENTRICULAR ACTIVATION SIMULATION AND SURFACE ECG REGISTRATION

CROSS-REFERENCE TO RELATED APPLICATIONS

This application represents the national stage entry of PCT International Application No. PCT/US2012/023256 filed on Jan. 31, 2012, and claims the benefit of U.S. Provisional Patent Application Ser. No. 61/462,366 filed Feb. 1, 2011. The disclosure of each of these applications is incorporated by reference for all purposes as if set forth in their entirety herein.

BACKGROUND OF THE INVENTION

The field of the invention is systems and methods for cardiac rhythm management. More particularly, the invention relates to systems and methods for performing cardiac resynchronization therapy in which adjustments to pacing control parameters are automatically made in relation to simulated and derived models of cardiac electrical activity, such as simulated and derived models of global cardiac electrical activity.

Left ventricular conduction delay due to bundle branch block causes regional heterogeneity in contraction and stretch, or asynchrony, which reduces pump function and stimulates negative left ventricular remodeling, such as increased chamber volumes. Experimental models have demonstrated a direct linkage between left ventricular electrical activation, cardiac mechanics, and remodeling. The conceptual basis of multisite pacing, which is also referred to as cardiac resynchronization therapy ("CRT") or biventricular pacing, for asynchronous heart failure is to minimize ventricular conduction delay, which reduces contractile asynchrony and improves chamber mechanics. Resynchronization of electromechanical activation induces so-called "reverse" remodeling, characterized by ventricular volume reductions, and improved pump function, characterized by increased ventricular ejection fraction. Reverse remodeling is associated with reduced heart failure morbidity and mortality. However, up to one-third of patients do not improve following CRT.

The translational mechanism for reverse volumetric remodeling in response to multisite pacing for asynchronous heart failure is ventricular activation wavefront fusion, which is evident on the paced 12-lead surface ECG. Presence of ventricular activation wavefront fusion predicts increased probability of reverse remodeling, whereas absence of wavefront fusion predicts reduced probability of remodeling, regardless of baseline substrate conditions.

Unfavorable substrate conditions, such as high myocardial scar volume or small amounts of ventricular conduction delay, cannot be modified by pacing techniques. In contrast, pacing strategies can be readily adapted to modify ventricular activation, and such instructions can be implemented automatically in the fully ambulatory patient having a cardiac implantable electrical device ("CIED"). Recent experimental evidence indicates that only two-thirds of CIED patients have paced surface ECG evidence of ventricular activation wavefront fusion during conventional CRT. This implies that failure to correct ventricular conduction delay, despite conventional CRT pacing, contributes significantly to volumetric remodeling non-response.

The limitation of existing CIED approaches to automatic or semi-automatic adjustment of pacing control systems for CRT is that they rely solely on limited device-based measurements that have not been correlated with improvement in any clinical outcome measure, most notably, reverse volumetric remodeling.

It would therefore be desirable to provide a system and method for generating patient-specific cardiac resynchronization therapy pacing control parameters that more accurately result in ventricular activation wavefront fusion as characterized by global ventricular activation patterns.

SUMMARY OF THE INVENTION

The present invention overcomes the aforementioned drawbacks by providing a system and method for cardiac resynchronization therapy ("CRT") in which a model of baseline cardiac electrical activity, such as a model of global baseline cardiac electrical activity derived from various surface electrocardiograph ("ECG") signals, is utilized to automatically adjust pacing control parameters of a cardiac implantable electrical device ("CIED") are provided. The baseline model is modified with simulated pacing control parameters in an iterative fashion until ventricular electrical asynchrony is minimized. The simulated pacing control parameters resulting in the minimum ventricular electrical asynchrony are used to generate an updated model of ventricular activation, and this updated model is used to generate control parameters for the CIED using a QRS glyph morphological framework.

It is an aspect of the invention to provide a method for delivering cardiac resynchronization therapy to a patient's heart with a cardiac rhythm management ("CRM") device. Signals representing baseline cardiac electrical activity in the patient's heart are acquired using electrocardiograph surface-lead electrodes, and a baseline model of ventricular conduction is formed using these signals. The baseline model is iteratively modified in order to minimize ventricular electrical asynchrony. From this iteratively modified baseline model, an updated model of global ventricular conduction that is indicative of ventricular activation wavefront fusion is generated. This updated model is then converted into pacing control parameters for the CRM device using a QRS hieroglyph morphological framework.

It is another aspect of the invention to provide a cardiac implantable electrical device ("CIED") for delivering cardiac resynchronization therapy to a patient's heart. The CIED includes an input for receiving signals indicative of baseline cardiac electrical activity in the heart from electrocardiography surface leads, an impulse delivery system for delivering electrical impulses to the heart in order to provide cardiac resynchronization therapy to the heart, a memory for storing pacing control parameters, and a processor in communication with the memory. The processor is configured to receive the signals representing baseline cardiac electrical activity in the patient's heart, form a baseline model of ventricular conduction using the received signals, iteratively modify the baseline model to minimize ventricular electrical asynchrony, generate an updated model of global ventricular conduction that is indicative of ventricular activation wavefront fusion using the iteratively modified baseline model, convert the updated model into pacing control parameters using a QRS hieroglyph morphological framework, and communicate with the impulse delivery system to provide cardiac resynchronization therapy to the heart in accordance with the pacing control parameters.

It is yet another aspect of the invention that real-time patient-specific simulations of cardiac electrical activation during multisite pacing may be used to identify the optimal conditions for generating maximum evidence of ventricular activation wavefront fusion.

It is yet another aspect of the invention that the aforementioned simulations rely on models of cardiac electrical activation that can be related to specific electrocardiography ("ECG") registrations on the body surface ("forward solution").

It is yet another aspect of the invention that body surface ECG signals can be related to cardiac electrical activation ("inverse solution").

It is yet another aspect of the invention that, using an "inverse solution," the baseline ventricular activation sequence is duplicated to form a baseline model of ventricular conduction.

It is yet another aspect of the invention that this baseline ventricular activation sequence model may be iteratively modified with pacing simulations of cardiac resynchronization therapy ("CRT") to generate maximum evidence of ventricular activation wavefront fusion.

It is yet another aspect of the invention that the final best-fit activation wavefront fusion simulation may be used to generate a "forward solution" for the corresponding unique surface ECG registration of global ventricular activation.

It is yet another aspect of the invention that the patient-specific simulation and modeling process is conducted in real-time by linking the simulation software and surface ECG to the CIED programmer.

It is yet another aspect of the invention that the final parameters of the inverse solution for baseline ventricular activation are stored in a registry on the CIED and/or CIED programmer.

It is yet another aspect of the invention that a registry of critical timing parameters, such as monochamber ventricular timing, cross-chamber ventricular timing, cross-chamber atrial-ventricular timing, varying stimulation strength and pulse duration, and others known to those skilled in the art, corresponding to each forward solution pacing simulation are automatically stored in a registry on the CIED and/or CIED programmer.

It is yet another aspect of the invention that these registries can be subsequently retrieved so that any desired set of critical timing control parameters generated by the simulations can be recalled, modified and implemented at a later date without necessarily recreating the inverse and forward solution processes.

It is yet another aspect of the invention that, in the event that the QRS glyph signature for ventricular activation fusion generated by the forward solution process cannot be suitably duplicated by CIED-based EGM surrogates, CIED operation could be instructed by implementing the critical timing parameters that generated activation wavefront fusion derived from the forward solution, which are stored in the settings registry. In this case, periodic automatic updates to critical control parameters could be achieved by repeating the inverse and forward solution simulation processes, rather than automatically using CIED-based EGM surrogates.

It is yet another aspect of the invention that the corresponding surface ECG registration can be transferred to CIED-based surface ECG surrogates in the form of multiple, complementary intracardiac, far-field (including body surface) EGM QRS glyphs, and the resulting CIED EGM QRS glyph template patterns can be used to continuously adapt pacing control parameters to guarantee optimal global ventricular activation wavefront fusion on a continuous (e.g., beat-to-beat) or nearly continuous basis.

It is yet another aspect of the invention that these enhancements provide additional advantages including patient-specific real-time ventricular activation sequencing; the ability to specifically model the effects of different pacing stimulation sites, timing relationships, and substrate conditions on ventricular activation sequencing; the ability to anticipate timing requirements necessary for achieving maximum evidence of ventricular activation wavefront fusion; the ability to directly transfer to body surface ECG registration facilitating identification and selection of pivotal CIED QRS glyph template patterns used to automatically adapt and update critical pacing control parameters to guarantee global ventricular activation wavefront fusion; and the ability to supplement and/or eliminate the conventional 12-lead surface ECG for ventricular activation sequencing analysis.

It is another aspect of the invention to provide a method for delivering cardiac resynchronization therapy to a patient's heart with a CIED for CRM. Pacing control and timing parameters used to direct the therapy are continuously and automatically adjusted using a model of cardiac electrical activity, such as a model of global cardiac electrical activity that is derived from baseline and paced surface electrocardiography signals. Exemplary timing parameters include atrio-ventricular intervals ("AVIs"), such as intrinsic AVIs ("iAVI"), pacemaker AVIs ("pAVI"), and effective AVIs ("eAVI").

It is yet another aspect of the invention to provide a method for automatically increasing atrial sensitivity of a CIED to overcome failure to achieve maximum evidence of ventricular activation wavefront fusion during multisite pacing and to reduce the risk of left ventricular filling abnormalities, such as diastolic dysfunction, without compromising maximal evidence of ventricular activation wavefront fusion.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Conventional cardiac pacing with implanted cardiac rhythm management ("CRM") devices, such as pacemakers and implantable cardioverter-defibrillators ("ICDs") with pacing functionality, involves delivering electrical pacing pulses to a patient's heart via intracardiac electrodes that are in electrical contact with desired portions of the heart. The CRM device is usually implanted subcutaneously on the patient's chest.

Figure 1:
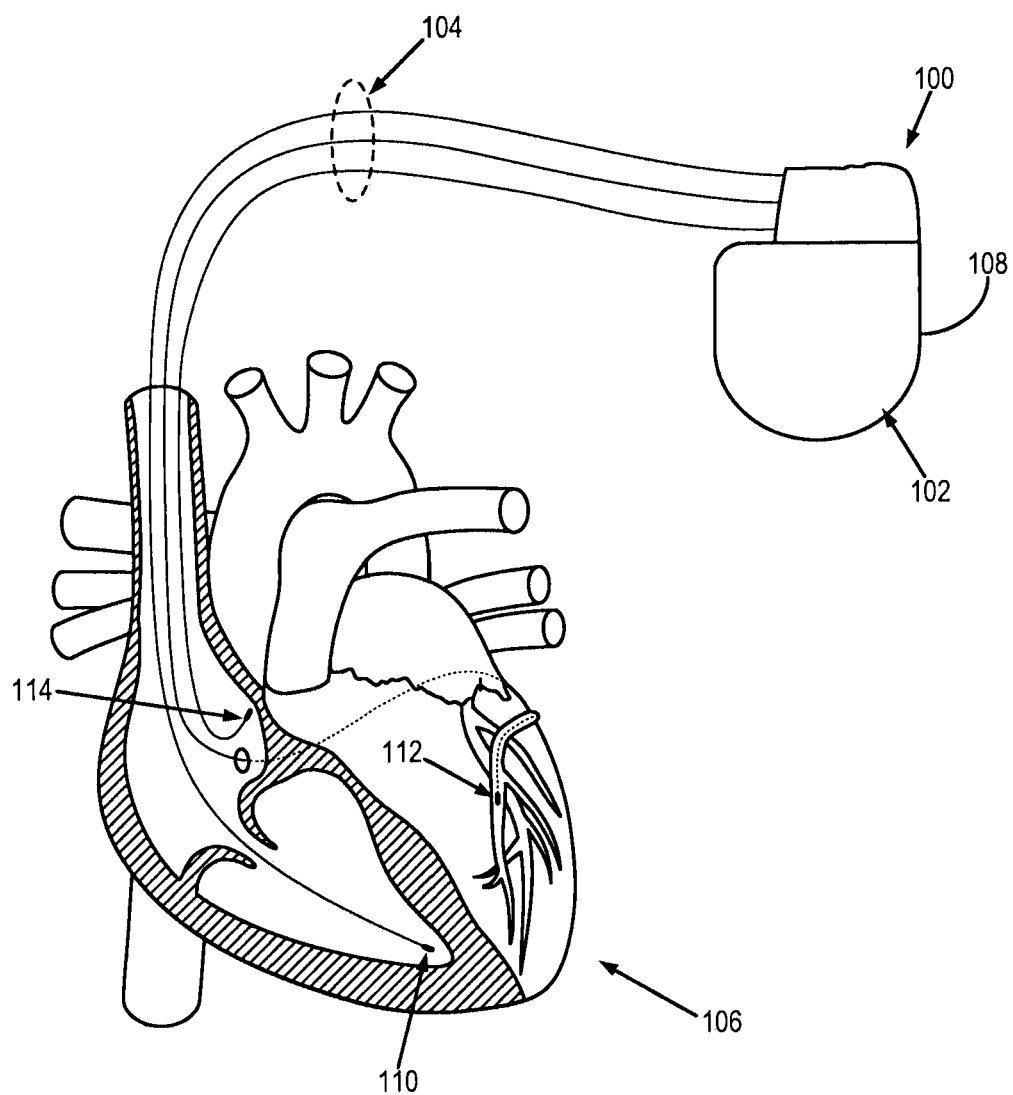
FIG. 1 is a pictorial representation of an exemplary cardiac implantable electronic device ("CIED") for cardiac rhythm management ("CRM") employed when practicing embodiments of the present invention.

Referring now to FIG. 1, an exemplary cardiac implantable electrical device ("CIED") 100 utilized for cardiac resynchronization therapy ("CRT") is illustrated. Such an exemplary CIED 100 includes an implantable pulse generator 102 that is in electrical communication with an intracardiac lead system 104.

Portions of the intracardiac lead system 104 may be inserted into the patient's heart 106 by way of the vessels of the upper venous system, such as the superior vena cava. The intracardiac lead system 104 includes one or more electrodes configured to produce an electrogram ("EGM") signal representing cardiac electrical activity sensed at the location of the electrode, between spatially separated electrodes, or between various combinations of electrodes and a housing 108 of the pulse generator 102, or to deliver pacing electrical pulses to the location of the electrode. Optionally, the intracardiac lead system 104 may include one or more electrodes configured to sense physiological parameters, such as cardiac chamber pressure or temperature.

The lead system 104 may include one or more intracardiac electrodes 110-114 positioned in, on, or about one or more heart chambers for sensing electrical signals from the patient's heart 106 and delivering pacing pulses to the heart 106. The intracardiac electrodes 110-114, such as those illustrated in FIG. 1, may be used to sense electrical activity in or pace one or more chambers of the heart, including the left ventricle, the right ventricle, the left atrium, and the right atrium. The lead system 104 may include one or more defibrillation electrodes for delivering cardioversion/defibrillation electrical shocks to the heart.

The pulse generator 102 includes circuitry for detecting cardiac arrhythmias and controlling pacing or defibrillation therapy in the form of electrical stimulation pulses or shocks delivered to the heart 106 through the lead system 104. The housing 108 of the pulse generator 102 also serves as a sensing electrode for recording far-field EGMs in combination with various selectable intracardiac electrodes 110-114. Such a controller is formed of a microprocessor in electrical communication with a memory for program and data storage. Other controller designs will be readily appreciated by those skilled in the art.

The controller is configured to operate the CIED 100 in a number of programmed modes, each programmed mode defining how pacing pulses are output in response to sensed cardiac electrical activity or in the absence of spontaneous cardiac electrical activity. Communications circuitry is also provided for facilitating communication between the controller and an external communication device, such as, for example, a portable or bed-side communication station, patient-carried/worn communication station, or external programmer. The communications circuitry may also facilitate unidirectional or bidirectional communication with one or more implanted; external; cutaneous or subcutaneous physiologic or non-physiologic sensors; patient-input devices; or information systems.

The controller controls the overall operation of the CIED 100 in accordance with programmed instructions stored in memory. The controller interprets electrogram signals sensed from the intracardiac electrodes 110-114, and far-field electrodes formed with the housing 108 of the pulse generator 102, and controls the delivery of pacing electrical pulses in accordance with a programmed pacing mode. The sensing circuitry of the CIED 100 generates multiple atrial, ventricular, and far-field electrogram signals, alone and in various combinations, from the voltages sensed by the electrodes of a particular channel. An electrogram is a device-based recording of local, regional or global cardiac electrical activity that is analogous to a surface ECG and indicates the time course and amplitude of cardiac depolarization that occurs during either an intrinsic or paced beat.

A morphological framework that provides direct, comparative analysis of EGMs acquired with a CIED and electrocardiograms acquired with an electrocardiograph ("ECG") device employing a surface-lead system was previously presented in co-pending Patent Application Number PCT/US10/42337, filed on Jul. 16, 2010, and entitled, "System and Method for Automated Adjustment of Cardiac Resynchronization Therapy Control Parameters," which is herein incorporated by reference in its entirety. This morphological framework includes a model of cardiac electrical activity formed from ECGs acquired before and after pacing with a CRM device. Thus, the model conveys information pertaining to abnormal baseline global cardiac electrical activity, changes in global cardiac electrical activity effectuated by a CRM device, and desirable global cardiac electrical activity that maximizes ventricular activation wavefront fusion, thereby guaranteeing maximum odds of improvement in cardiac pump function. While the EGMs do not share the same point-of-view as the surface-lead system commonly employed by an ECG device to record global cardiac activity, by way of the morphological framework, the model of cardiac electrical activity can be directly compared to EGMs recorded by a CIED. Therefore, multiple CIED EGMs function as morphologic surrogates for surface ECG measures of global cardiac electrical activity.

Figure 2:
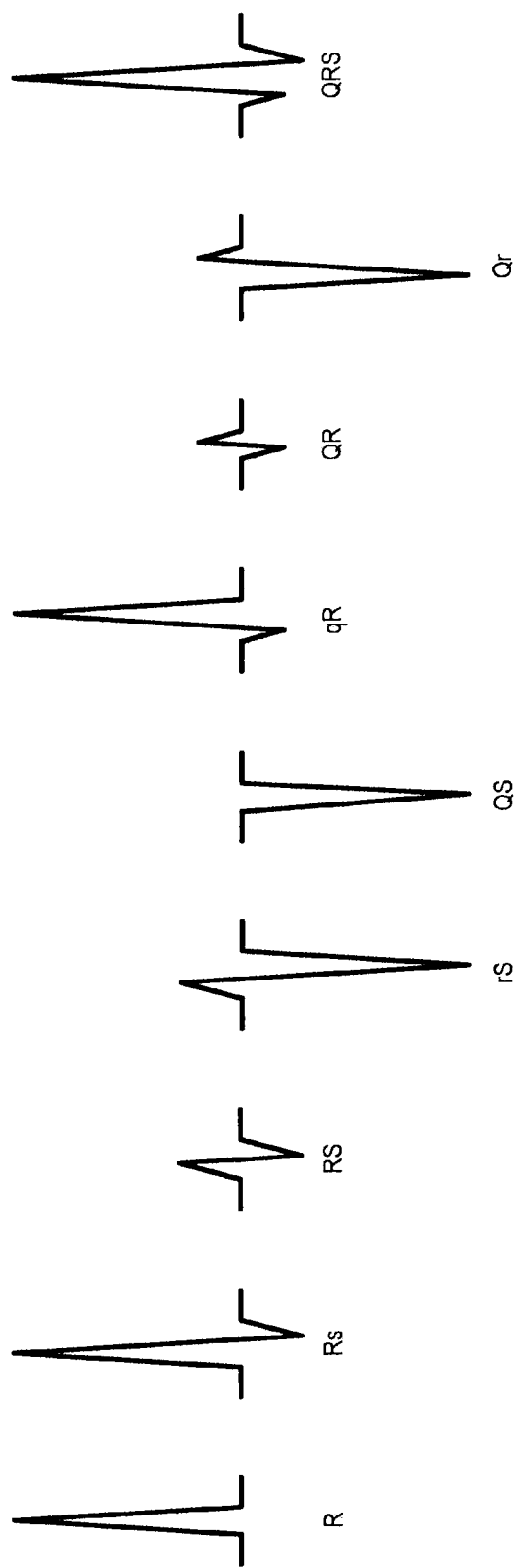
FIG. 2 is a pictorial illustration of a set of exemplary QRS complex hieroglyphs, or "glyphs," that form a morphological framework for correlating CIED measurements of cardiac electrical activity with surface ECG measurements of global cardiac electrical activity.

The morphological framework is referred to as a QRS hieroglyphic framework for ventricular activation pattern comparisons. Briefly, the pre-pacing and post-pacing QRS complex in each surface lead is deconstructed into four possible waveform elements: R, S, Q, and QS. Absolute amplitudes in millivolts ("mV") and durations in milliseconds ("ms") of all elements of each QRS complex are used to characterize specific activation patterns. Ventricular activation in each surface lead can be characterized by nine possible patterns, or QRS hieroglyphs ("glyphs"), as described below in Table 1 and illustrated in FIG. 2.

TABLE 1

| Glyph | Description |
| --- | --- |
| R | Only R-wave present |
| RS | R-wave and S-wave present with equal amplitude |
| Rs | R-wave and S-wave present, R-wave with greater amplitude |
| rS | R-wave and S-wave present, S-wave with greater amplitude |
| QS | Q-wave and S-wave present with equal amplitude |
| qR | Q-wave and R-wave present, R-wave with greater amplitude |
| QR | Q-wave and R-wave present with equal amplitude |
| Qr | Q-wave and R-wave present, Q-wave with greater amplitude |
| QRS | Q-wave, R-wave, and S-wave are all present |

Typical ventricular activation during left bundle branch block ("BBB") is registered as right-to-left in the frontal plane, anterior-to-posterior in the horizontal plane, and variable axis on the surface ECG. By way of example for characterizing cardiac electrical activity recorded with surface leads in the QRS hieroglyph framework, this ventricular conduction block produces a stereotypic hieroglyphic signature with dominant positive forces in surface leads I, aVL (glyphs: R, Rs), negative forces in aVR (glyph: QS), variable forces in II, III, AVF (glyphs: R, Rs, rS, QS), dominant negative forces in V1-V2 (glyphs: QS, rS), transition in V3-V5 (glyphs: rS into Rs, R) and dominant positive forces in V5-V6 (glyphs: R, Rs). Other characteristic QRS hieroglyphic signatures can be similarly constructed for different forms of ventricular conduction block.

The process for plotting a patient-specific solution to generate maximum evidence of ventricular activation wavefront fusion is conducted in consecutive steps. Generally, the first step includes duplicating a baseline condition of the patient. For example, the baseline condition may include a baseline conduction disturbance to be corrected. The simulation of this baseline ventricular activation sequence is referred to as an "inverse solution." The baseline simulation may be achieved by modifying a model simulation of normal ventricular conduction using analysis of the patient's baseline surface ECGs. These unique body surface ECG signals may be used to specify the simulation of baseline cardiac electrical activation.

As will be described below, the baseline model is iteratively modified to generate delay in left ventricular activation. While the baseline simulation is generated from ECG signals, the modifications to the baseline model may be assessed by analyzing the effects of these changes on the QRS hieroglyphic signature of the baseline model.

In general, the process then generates a forward solution for surface ECG registration corresponding to the final model of activation wavefront fusion. The ECG QRS glyph patterns generated by the forward solution and corresponding to the simulated paced ventricular activation sequence which minimizes ventricular electrical asynchrony are then used to instruct and update CIED timing operations.

Figure 3:
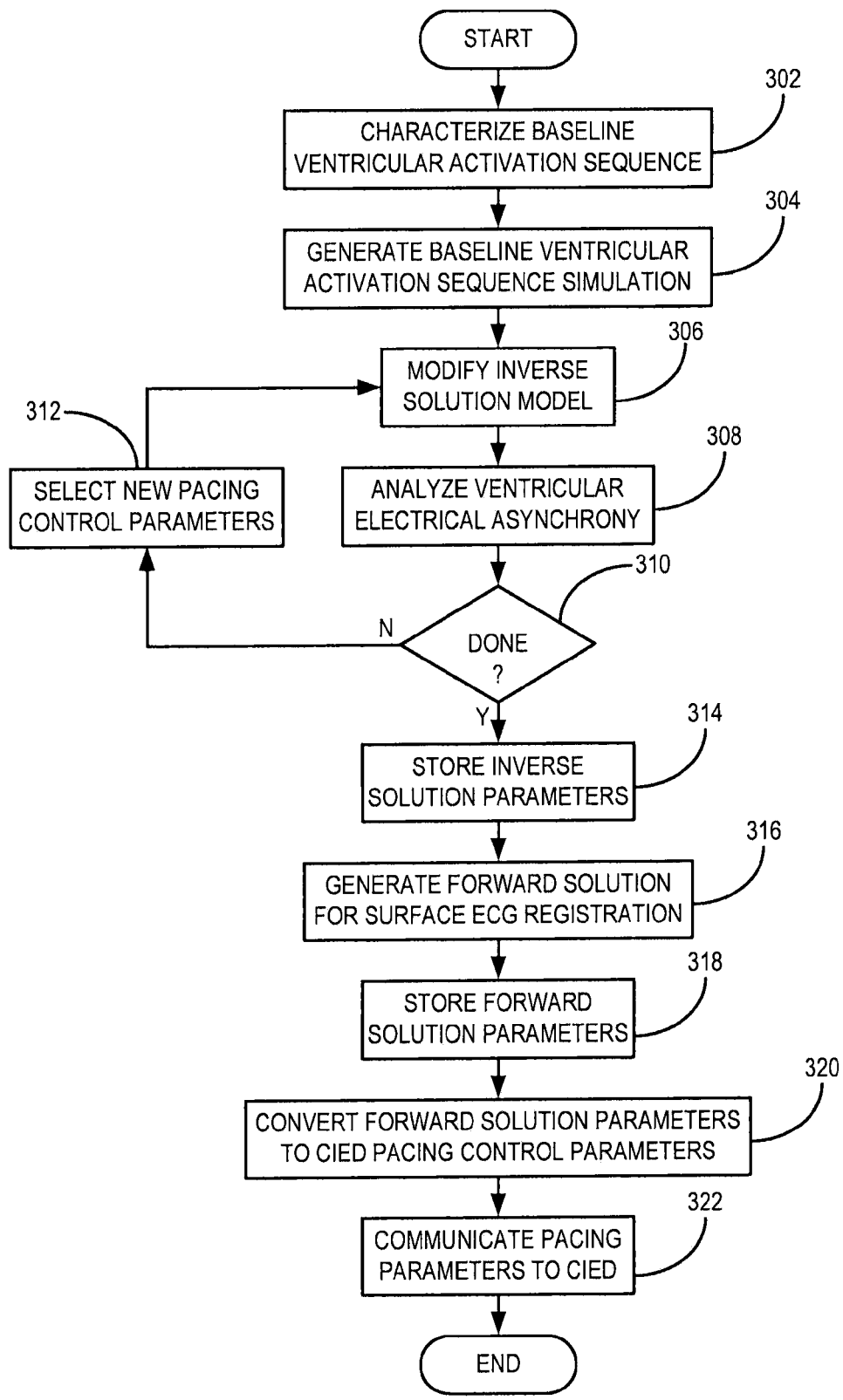
FIG. 3 is a flowchart setting forth the steps of an example of a method for generating pacing control parameters for cardiac resynchronization therapy in accordance with some embodiments of the invention.

Referring now to FIG. 3, a flowchart setting forth the steps of an example of a method for generating pacing control parameters for cardiac resynchronization therapy is illustrated. The method begins with the analysis and characterization of a patient's baseline ventricular activation sequence, as indicated at step 302. For example, surface ECG leads can be used to characterize this baseline ventricular activation sequence by identifying key components of the ventricular activation sequence. Examples of these key components include right ventricular activation time ("VAT"), left VAT, scar volume, QRS duration, and electrical axis.

Following the characterization of the baseline ventricular activation sequence, a baseline model is generated, as indicated at step 304. This baseline model duplicates the characterized baseline ventricular activation sequence, and the goal of producing such a model is to create an inverse solution simulation that duplicates the precise patient-specific QRS hieroglyphic signature for global baseline ventricular conduction. Preferably, the baseline model will minimally satisfy the following related conditions. First, the baseline model will include an identical QRS hieroglyphic signature on the surface ECG with particular attention to pivotal leads. Second, the baseline model will include identical left ventricular activation time ("VAT") and right VAT as the characterized baseline ventricular activation sequence, as determined by analysis of the surface ECG. And third, the baseline model will include the duplication of regional myocardial scar distributions, which interact with activation wavefront propagation, as determined by analysis of the surface ECG.

It is also preferable that the baseline model provide quantification of left ventricular scar volume corresponding to the QRS score for left bundle branch block ("BBB"). The effects of myocardial scar on left BBB surface registration translate as specific QRS hieroglyphic signatures, manifest as unopposed rightward electrical forces by infarct region. The effects of left ventricular scar on the baseline ventricular activation simulation are accounted for by incorporating low propagation velocity regions and other measures by specific anatomic location. Similar information for specific anatomic distribution of scar and total ventricular scar volume could be generated by other known methodologies, including cardiac magnetic resonance imaging; ultrasound imaging, such as echocardiography; and catheter-based endocardial or epicardial electrical activation mapping. The exact technique for measuring scar volume and distribution is not of primary importance as long as it provides the correct anatomic designation for the ventricular activation simulations.

In the baseline model, one or more regions of delay of varying magnitudes may be necessary to achieve a duplication of the patient-specific ventricular conduction pattern. A common characteristic of this arrangement is slow propagation of the activation wavefront on the left side of the interventricular septum. The initial point of delay varies substantially between patients and can be varied within the simulation based on analysis of the ECG or other sources of physiologic information regarding ventricular electromechanical activation. It is expected that the latest activated segment will most often reside in the posterior-basal left ventricle, consistent with physiologic observations, unless modified by intervening scar or other disruptions to wavefront propagation, or other sources of physiologic information regarding ventricular electromechanical activation. The time from left ventricular breakout (earliest point of electrical activation) to latest activation should closely approximate the left VAT determined by surface ECG analysis or other measuring techniques known to those skilled in the art.

As indicated at step 306, the baseline model is subsequently and iteratively modified using different sets of simulated pacing control parameters. These modifications are applied to seek the generation of ventricular activation wavefront fusion. The anatomic location of the simulated pacing stimulation site(s) correspond to the known or desired position of the stimulating electrode(s) on the endocardial or epicardial surface of the individual patient. By way of example, the pacing simulations performed on the baseline model may include various manipulations of monochamber ventricular timing, cross-chamber ventricular timing, cross-chamber atrial-ventricular timing, and varying stimulation strength and pulse duration. Methods for these pacing simulations are achievable with the CIED and known to those skilled in the art.

The modified baseline model is analyzed to determine whether ventricular electrical asynchrony is minimized using the simulated pacing control parameters, as indicated at step 308. Examples of methods for minimizing ventricular electrical asynchrony include monochamber ventricular pacing, biventricular pacing at single sites in each chamber, and biventricular pacing at multiple sites in each chamber. The pacing site arrangement employed in the specific patient is duplicated in the forward solution model, discussed below. Real-time analysis of the resulting ventricular activation wavefronts are analyzed until fusion is achieved. Fusion activation is registered by a variety of criteria known to those skilled in the art. Thus, if ventricular electrical asynchrony is not minimized by the simulated pacing control parameters, as determined at decision block 310, then a new set of pacing control parameters is selected at step 312 and the baseline model is further modified using these new pacing control parameters. When the simulated pacing control parameters that minimize ventricular electrical asynchrony are determined, this set of parameters is stored as inverse solution conditions in the CIED or programmer memory, as indicated at step 314.

The stored pacing control parameters and inverse solution conditions are used next to generate a forward solution for surface ECG registration, as indicated at step 316. In general, the forward solution for surface ECG registration corresponds to a final model of ventricular activation wavefront fusion. The forward solution pacing control parameters are then stored in the CIED or programmer memory, as indicated at step 318.

It is expected that wavefront opposition and reversal during multisite pacing will yield predictable ECG-evidence of wavefront fusion. This evidence may be broadly characterized by the following conditions. One condition is an expected change in frontal plane electrical axis, such as normal or left axis deviation changing to right axis deviation. This change in frontal plane electrical axis indicates reversal of activation in the frontal plane. Another condition is expected changes in QRS hieroglyphic signatures. For example, rightward forces may emerge in leads with dominant leftward forces, which would indicate reversal of activation in the frontal plane. Such a change in QRS glyph signatures would manifest as an R glyph in leads I and aVL changing to a qR, QR, or QS glyph. As another example, anterior forced may emerge in leads with dominant posterior forces, which indicated reversal of activation in the horizontal place. Such a change in QRS glyph signatures would manifest as a QS glyph in lead V1 changing to an rS, RS, Rs, or R glyph; as a QS or rS glyph in lead V2 changing to an RS, Rs, or R glyph; and as an rS or RS glyph in lead V3 changing to an Rs or R glyph.

An alternate way of characterizing evidence for ventricular fusion is using regional or global measures of change in maximum R-wave amplitude in the expected direction indicating activation wavefront reversal before and after pacing.

The expected changes in local and regional QRS hieroglyphic signatures are most pronounced in surface ECG leads I, aVL, V1, and V2, which are designated pivotal leads. Using these pivotal leads, global ventricular activation can be characterized in the orthogonal frontal and horizontal planes. Leads I and aVL indicate global activation in the right-to-left direction (frontal plane) and leads V1 and V2 indicate global activation in the anterior-to-posterior direction (horizontal plane). Therefore, another alternate approach to analysis of global ventricular activation would limit the surface ECG input to a reduced lead set without compromising accuracy. This lead set could consist of 1-2 leads for evaluating activation wavefront reversal in the frontal plane (1, aVL) and 1-2 leads in the horizontal plane (V1, V2).

By way of example, the aforementioned changes in QRS hieroglyphic signatures were greatest in lead I for the frontal plane and in lead V1 for the horizontal plane. Therefore, an even simpler surface ECG lead set including only pivotal leads I and V1 could provide sufficient observational power for detecting activation wavefront reversal in two orthogonal planes.

As indicated at step 320, the forward solution parameters are translated into CIED pacing control parameters using the QRS glyph morphological framework discussed above. This patient-specific simulation and modeling process is conducted in real-time by linking the simulation software and surface ECG to the CIED programmer. As an example, a CIED programmer commonly maintains a continuous wired or wireless telemetry link to an implanted CIED. Included in this process is the generation of morphology templates that can serve as surrogates for QRS hieroglyphic signatures indicative of ventricular activation fusion.

The final parameters of the inverse solution for baseline ventricular activation are stored in a registry on the CIED and/or CIED programmer. These would be available for future simulation attempts and updates to the forward solution parameters as desired, or in response to an important change in patient, or patient-specific substrate conditions. Similarly, a registry of critical timing parameters (mono-chamber ventricular timing, cross-chamber ventricular timing, cross-chamber atrial-ventricular timing, varying stimulation strength and pulse duration, and others known to those skilled in the art) corresponding to each forward solution pacing simulation are automatically stored in a registry on the CIED and/or CIED programmer. This registry can be subsequently retrieved so that any desired set of critical timing control parameters generated by the simulations can be recalled, modified and implemented at a later date without necessarily recreating the inverse and forward solution processes.

The QRS glyph templates are communicated to the CIED or programmer memory, as indicated at step 322, and used for operation of the CIED during cardiac rhythm management. By way of example, the QRS glyph templates are used to automatically and periodically adjust pacing control parameters of the CIED. In the event that the QRS glyph signature for ventricular activation fusion derived from the forward solution cannot be suitably duplicated by the CIED-based surrogates, the stored pacing control parameters calculated from the forward solution may be used to control operation of the CIED. In this case, periodic automatic updates to critical control parameters could be achieved by repeating the inverse and forward solution simulation processes, rather than automatically using CIED-based EGM surrogates.

Thus, systems and methods for generating highly accurate and informed patient-specific simulations of ventricular activation wavefront propagation before and after single or multisite pacing for CRT have been provided. Generally, a pre-pacing 12-lead ECG is used to create an inverse solution for the ventricular activation sequence associated with the baseline ventricular conduction disturbance. The simulated ventricular activation sequence is then manipulated by pacing stimulation to demonstrate activation wavefront fusion. The fusion simulation is then used to create a forward solution during optimal pacing on the 12-lead ECG. QRS hieroglyphic analysis of the paced ECG identifies the patient-specific activation sequence that is subsequently orchestrated through automatic device timing instructions.

QRS hieroglyphic analysis is used for characterization of the patient-specific baseline ventricular activation sequence, and accurate numerical quantification of key elements of the baseline ventricular activation sequence is performed. Examples of key elements of the baseline ventricular activation sequences include right VAT, left VAT, scar volume, QRS duration, electrical axis, and so on. A 12-lead surface ECG is used for deriving and quantifying these key elements. Anatomically accurate knowledge of the left ventricular and right ventricular stimulation site(s) are achieved. To guide the generation of pacing control parameters, a numerically quantifiable endpoint of the modeling process, defined as minimization of ventricular electrical asynchrony, is used and manifested as ventricular activation wavefront fusion.

The systems and methods of the present invention are used to identify a patient-specific, post-pacing ECG QRS glyph pattern corresponding to the simulated ventricular activation sequence that minimizes ventricular electrical asynchrony. The identification of this QRS glyph pattern is performed in order to automatically instruct and periodically update CIED timing operation to maximize the odds of reverse left ventricular remodeling, improved left ventricular pump function, and composite clinical improvement during CRT.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for delivering cardiac resynchronization therapy to a patient's heart with a cardiac rhythm management (CRM) device, the steps of the method comprising:
 a) acquiring signals representing baseline cardiac electrical activity in the patient's heart using electrocardiograph surface-lead electrodes;
 b) forming a baseline model of ventricular conduction using the signals acquired in step a);
 c) iteratively modifying the baseline model formed in step b) to minimize ventricular electrical asynchrony;
 d) generating an updated model of global ventricular conduction that is indicative of ventricular activation wavefront fusion using the iteratively modified baseline model; and
 e) converting the updated model into pacing control parameters for the CRM device using a QRS hieroglyph morphological framework.

2. The method as recited in claim 1 in which step b) includes characterizing a baseline ventricular activation sequence in the signals acquired in step a).

3. The method as recited in claim 2 in which the baseline ventricular activation sequence is characterized by identifying components of a ventricular activation sequence.

4. The method as recited in claim 3 in which the identified components include right ventricular activation time (VAT), left VAT, scar volume, QRS duration, and electrical axis.

5. The method as recited in claim 2 in which the baseline model formed in step b) duplicates a patient-specific QRS hieroglyphic signature for global baseline ventricular conduction indicated by the ventricular activation sequence.

6. The method as recited in claim 1 in which the baseline model is iteratively modified in step c) using simulated pacing control parameters.

7. The method as recited in claim 6 in which the simulated pacing control parameters include monochamber ventricular timing, cross-chamber ventricular timing, cross-chamber atrial-ventricular timing, and varying stimulation strength and pulse duration.

8. The method as recited in claim 1 in which step e) includes generating QRS glyph templates that are surrogates for QRS hieroglyphic signatures indicative of ventricular activation fusion.

9. A cardiac implantable electrical device for delivering cardiac resynchronization therapy to a patient's heart, the cardiac implantable electrical device comprising:
 an input for receiving signals indicative of baseline cardiac electrical activity in the heart from electrocardiography surface leads;
 an impulse delivery system for delivering electrical impulses to the heart in order to provide cardiac resynchronization therapy thereto;
 a memory for storing pacing control parameters;
 a processor in communication with the memory, the processor being configured to:
  receive the received signals representing baseline cardiac electrical activity in the patient's heart;
  form a baseline model of ventricular conduction using the received signals;
  iteratively modify the baseline model to minimize ventricular electrical asynchrony;
  generate an updated model of global ventricular conduction that is indicative of ventricular activation wavefront fusion using the iteratively modified baseline model;
  convert the updated model into pacing control parameters using a QRS hieroglyph morphological framework; and
  communicate with the impulse delivery system to provide cardiac resynchronization therapy to the heart in accordance with the pacing control parameters.

10. The cardiac implantable electrical device as recited in claim 9 in which the processor is further configured to form a baseline model of ventricular conduction by characterizing a baseline ventricular activation sequence in the received signals.

11. The cardiac implantable electrical device as recited in claim 10 in which the processor is configured to characterize the baseline ventricular activation sequence by identifying components of a ventricular activation sequence.

12. The cardiac implantable electrical device as recited in claim 11 in which the identified components include right ventricular activation time (VAT), left VAT, scar volume, QRS duration, and electrical axis.

13. The cardiac implantable electrical device as recited in claim 10 in which the processor is configured to form the baseline model by duplicating a patient-specific QRS hieroglyphic signature for global baseline ventricular conduction indicated by the ventricular activation sequence.

14. The cardiac implantable electrical device as recited in claim 9 in which the processor is configured to iteratively modify the baseline model using simulated pacing control parameters.

15. The cardiac implantable electrical device as recited in claim 14 in which the simulated pacing control parameters include monochamber ventricular timing, cross-chamber ventricular timing, cross-chamber atrial-ventricular timing, and varying stimulation strength and pulse duration.

16. The cardiac implantable electrical device as recited in claim 9 in which the processor is configured to generate the updated model by generating QRS glyph templates that are surrogates for QRS hieroglyphic signatures indicative of ventricular activation fusion.

* * * * *